United States Patent [19]

Graf et al.

[11] Patent Number: 4,698,434
[45] Date of Patent: Oct. 6, 1987

[54] PREPARATION OF HYDROXYMETHYLIMIDAZOLES

[75] Inventors: Fritz Graf, Speyer; Leopold Hupfer, Friedelsheim, both of Fed. Rep. of Germany

[73] Assignee: BASF Aktiengesellschaft, Ludwigshafen, Fed. Rep. of Germany

[21] Appl. No.: 907,585

[22] Filed: Sep. 15, 1986

[30] Foreign Application Priority Data

Sep. 25, 1985 [DE] Fed. Rep. of Germany ....... 3534083

[51] Int. Cl.[4] ............................................ C07D 233/64
[52] U.S. Cl. ................................ 548/342; 548/337; 548/339
[58] Field of Search .................. 548/342, 337, 339

[56] References Cited

U.S. PATENT DOCUMENTS 4,189,591  2/1980  Mueller et al. ...................... 548/342
4,275,216  6/1981  Hubert-Brierre ................... 548/342

FOREIGN PATENT DOCUMENTS 4534  7/1981  European Pat. Off. ............ 548/342

OTHER PUBLICATIONS

H. Erlenmeyer et al., *Helvetica Chimica Acta* 31, (1948) 32–41.

*Primary Examiner*—Richard A. Schwartz
*Attorney, Agent, or Firm*—John H. Shurtleff

[57] ABSTRACT

Imidazoles which carry a hydroxymethyl radical on a carbon atom of the imidazole ring are prepared by treating a 1-hydroxymethylimidazole, which is unsubstituted in one or more of the positions 2, 4 and 5 of the imidazole ring, with an anion exchanger.

6 Claims, No Drawings

PREPARATION OF HYDROXYMETHYLIMIDAZOLES

The present invention relates to a novel process for the preparation of imidazoles which carry a hydroxymethyl radical on a carbon atom of the imidazole ring, by subjecting a 1-hydroxymethylimidazole to a rearrangement reaction over a basic ion exchanger.

4(5)-methyl-5(4)-hydroxymethylimidazole can be obtained, for example, by the process described in Helv. Chim. Acta 31, (1948), 38, by heating 4(5)-methylimidazole with formaldehyde in a bomb tube at 120° C. European Patent No. 4,534 and German Laid-Open Application No. DOS 2,934,925 disclose that 4(5)-methyl-5(4)-hydroxymethylimidazole can be prepared in a more advantageous manner if the reaction of 4(5)-methylimidazole with formaldehyde is carried out in an aqueous alkaline medium at pH 11–13 and at from 20° to 60° C., or in the presence of a strong base at from 30° to 95° C. The disadvantage of these processes is the involved working up procedure for separating off the bases required in the synthesis. In general, 4(5)-methyl-5(4)-hydroxymethylimidazole is obtained in the form of the hydrochloride.

The hydrochloride of 4(5)-methyl-5(4)-hydroxymethylimidazole can also be prepared by reacting 4(5)-methylimidazole with formaldehyde under superatmospheric pressure and at elevated temperatures in the presence of hydrochloric acid. Here too, the disadvantage is the involved working up procedure. Moreover, corrosion-resistant materials are required.

We have found that imidazoles which carry a hydroxymethyl radical on a carbon atom of the imidazole ring can be prepared in a substantially more advantageous manner if a 1-hydroxymethylimidazole which is unsubstituted in one or more of the positions 2, 4 and 5 of the imidazole ring is treated with anion exchanger. The novel process gives the hydroxymethylimidazoles in a particularly simple manner and in good yield and high purity.

Suitable starting materials are 1-hydroxymethylimidazoles which are unsubstituted in, for example, the 5(4)-position and may contain substituents, such as halogen, alkyl, hydroxyalkyl, nitro or phenyl in the 2- and 4(5)-positions. Examples of suitable alkyl or hydroxyalkyl radicals are methyl, ethyl, propyl, hexyl, decyl, hydroxymethyl, hydroxyethyl and hydroxypropyl. The phenyl radicals may be substituted, for example by halogen, such as fluorine, chlorine or bromine, or by nitro, methyl or ethyl. The starting materials may be structurally depicted by the formula

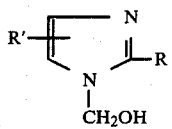

wherein R and R' are the substituents named above.

Examples of starting compounds are the following: 1-hydroxymethylimidazole, 4(5)-methyl-1-hydroxymethylimidazole, 2-methyl-1-hydroxymethylimidazole, 4(5)-nitro-1-hydroxymethylimidazole, 2- and 4(5)-phenyl-1-hydroxymethylimidazole, 2-isopropyl-1-hydroxymethylimidazole, 2,4(5)-dimethyl-1-hydroxymethylimidazole, 2- and 4(5)-ethyl-1-hydroxymethylimidazole and 4,5-d These starting compounds can be prepared, for example, by the process described in German Laid-Open Application No. DOS 2,825,547.

In the process of the invention, in which the hydroxymethyl radical migrates to one of the free positions 2, 4 or 5 of the imidazole ring, the 1-hydroxymethylimidazole is treated with the anion exchanger, for example for 0.1–100, preferably 1–50, hours at from 0° to 120° C., preferably from 30° to 70° C.

In the novel process, the 1-hydroxymethylimidazoles are advantageously used in the form of a solution in a solvent, and mixtures of solvents may also be used. Examples of suitable solvents are water, alcohols, such as methanol or ethanol, and ketones such as acetone or methyl ethyl ketone. For example, solutions which contain up to 85, preferably from 20 to 80, in particular from 50 to 75, % by weight of the imidazole compound are used. Solutions of the 1-hydroxymethylimidazoles in water, such as a 5–85% strength by weight aqueous solution, are preferably employed.

Suitable anion exchangers are all conventional basic ion exchangers, for example those based on styrene divinylbenzene or a polyamine condensate, such as the ion exchangers available commercially under the names DOWEX, AMBERLIT and LEWATIT. LEWATIT M 406 and DOWEX MSA are particularly useful. When used according to the invention the anion exchanger is not altered and can be used as often as desired.

The novel process is carried out, for example, as follows: a solution of the 1-hydroxymethylimidazole is passed, at from 40° to 80° C., for from two to five hours, through a tube filled with the anion exchanger. The hydroxymethylimidazole is isolated from the outflowing reaction solution in a conventional manner, for example by crystallization of the reaction solution, which, if necessary, has been concentrated by evaporation. The hydroxymethylimidazole can be obtained in pure form by washing, for example with acetone, or by recrystallization.

The hydroxymethylimidazoles obtainable by the process according to the invention are important intermediates, for example for the preparation of drugs.

EXAMPLE

A solution of 112 g of 4(5)-methyl-1-hydroxymethylimidazole in 45 ml of water is passed, at 60° C., for three hours, through a tube filled with 1,000 ml of anion exchanger. The anion exchanger available commercially under the name Lewatit ® M 504 is used for this purpose. The outflowing reaction solution, which contains 48.34% (75.9 g) of 4(5)-methyl-4(5)-hydroxymethylimidazole (67.77% yield), substantially solidifies on standing. The 4(5)-methyl-5(4)-hydroxymethylimidazole which has crystallized out is filtered off under suction and then freed from byproducts by washing with acetone; after drying, it has a melting point of 137°–138° C.

The aqueous mother liquor separated off is evaporated to dryness, and the residue is treated with the wash acetone obtained above, 12 g of a second fraction of 4(5)-methyl-5(4)-hydroxymethylimidazole of somewhat lower purity being obtained.

We claim:

1. A process for the preparation of an imidazole which contains a hydroxymethyl radical on a carbon atom of the imidazole ring, wherein a 1-hydroxymethylimidazole which is unsubstituted in one or more of the positions 2, 4 and 5 of the imidazole ring is treated with an anion exchanger.

2. A process as claimed in claim 1, wherein the treatment is carried out at from 0° to 120° C.

3. A process as claimed in claim 1, wherein the 1-hydroxymethylimidazole is used in the form of a solution in a solvent.

4. A process as claimed in claim 1, wherein a 5 -5% strength by weight aqueous solution of the 1-hydroxymethylimidazole is treated with the anion exchanger.

5. A process as claimed in claim 1, wherein the 1-hydroxymethylimidazole used is of the formula

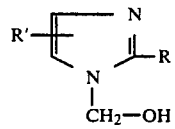

where R' is in the 4 or 5 position and R and R' are each hydrogen, halogen, alkyl, hydroxyalkyl, nitro or phenyl which may be substituted by halogen, nitro, methyl or ethyl.

6. A process as claimed in claim 1, wherein 4(5)-methyl-5(4)-hydroxymethylimidazole is prepared from 4(5methyl-1-hydroxymethylimidazole.

* * * * *

UNITED STATES PATENT AND TRADEMARK OFFICE
CERTIFICATE OF CORRECTION

PATENT NO. : 4,698,434
DATED : October 6, 1987
INVENTOR(S) : Fritz Graf and Leopold Hupfer It is certified that error appears in the above-identified patent and that said Letters Patent is hereby corrected as shown below:

Claim 4, line 1:  change "5 - 5%" to -- 5 - 85% --.

Claim 6, line 3:  change "4(5methyl" to -- 4(5)-methyl --.

Signed and Sealed this

Second Day of August, 1988

Attest:

DONALD J. QUIGG

Attesting Officer

Commissioner of Patents and Trademarks